United States Patent [19]

Mathiasmeier et al.

[11] Patent Number: 6,029,358
[45] Date of Patent: Feb. 29, 2000

[54] SOLID STATE DIGITAL ELECTRONIC SHOE SIZER

[75] Inventors: Michael L. Mathiasmeier; William E. Fullen, both of Houston, Tex.

[73] Assignee: Dwayne L. Mason, Houston, Tex.

[21] Appl. No.: 08/956,528

[22] Filed: Oct. 23, 1997

Related U.S. Application Data

[63] Continuation-in-part of application No. 08/526,669, Sep. 11, 1995, Pat. No. 5,729,905.

[51] Int. Cl.[7] .................................................. A61B 5/103
[52] U.S. Cl. ................................................................ 33/3 R
[58] Field of Search ............................. 33/3 A, 3 B, 3 C, 33/3 R, 511, 512; 128/779; 73/172, 774, 775, 776, 865.7, 862.07

[56] References Cited

U.S. PATENT DOCUMENTS

| | | | |
|---|---|---|---|
| 2,216,533 | 10/1940 | Kaplan | 33/3 C |
| 3,328,882 | 7/1967 | Blivice | 33/3 |
| 3,457,647 | 7/1969 | Cohen et al. | 33/3 R |
| 4,294,014 | 10/1981 | Baumann et al. | 33/3 C |
| 4,734,034 | 3/1988 | Maness et al. | 433/68 |
| 5,123,169 | 6/1992 | White et al. | 33/3 R |
| 5,128,880 | 7/1992 | White | 33/512 |
| 5,323,650 | 6/1994 | Fullen et al. | 128/779 |
| 5,361,133 | 11/1994 | Brown et al. | 33/515 |
| 5,729,905 | 3/1998 | Mathiasmeier et al. | 33/3 R |
| 5,790,256 | 8/1998 | Brown et al. | 33/3 R |

FOREIGN PATENT DOCUMENTS

| | | | |
|---|---|---|---|
| 284922 | 10/1988 | European Pat. Off. | 33/512 |
| 285989 | 10/1988 | European Pat. Off. | 33/3 R |

OTHER PUBLICATIONS

Brochure on Achilles Solid–State Electronic Shoe Sizer . . . The Fitting Solution, no date.

*Primary Examiner*—G. Bradley Bennett
*Attorney, Agent, or Firm*—Winstead Sechrest & Minick P.C.; Dwayne L. Mason

[57] ABSTRACT

The invention pertains to an apparatus for measuring a foot's length and width to correspond to a shoe size, utilizing digital distributed sensor arrays The apparatus is a low profile self-contained apparatus comprising a transducing medium, a microcontroller, a reference impedance element, a signal amplifier, digital distributed sensor arrays comprising vertical and horizontal traces and a display to generate and display foot sizing data. The shoe size is then calculated using a sizing algorithm with the results shown on a display which is connected to the output of the microcontroller unit.

22 Claims, 4 Drawing Sheets

SOLID STATE DIGITAL ELECTRONIC SHOE SIZER

This is a continuation-in-part application of application Ser. No. 08/526,669, entitled Foot Measuring Apparatus and Circuitry to Eliminate Multiplexers and Demultiplexers, filed Sep. 9, 1995, now U.S. Pat. No. 5,727,905, issued Mar. 24, 1998.

BACKGROUND OF THE INVENTION

1. Field of the Invention

This invention relates to an apparatus used to measure and size human feet as a guide to fitting mass produced footwear. More specifically, it applies to electronic, solid-state digital design intended primarily for self-service retail applications.

2. Prior Art

With the inception of mass produced footwear, it was recognized that an efficient means by which to match the individual foot to the closest available standard last was required to simplify selection and insure proper fit. This resulted in the manufacture and patenting of a wide variety of devices ranging from simple metering sticks to assorted electronic, mechanical, electromechanical designs and even highly complex three-dimensional imaging systems. Such methods are well documented as cited in U.S. Pat. Nos. 4,294,014, 5,323,650 and 5,123,169.

However, before evaluating such designs, a brief comment regarding the purpose and practicality of such a mechanism may help clarify the ensuing analysis. It should be noted that shoe sizing is not an exact science, primarily for two reasons. First, it is highly subjective in nature leading various manufacturers to place emphasis on different anatomical measurements such as ball girth, instep, waist and length in the last development. This is most evident by the fact that, while US manufacturers have more than ten designations governing width, European makers use length only. Second, although numerous sizing scales have been developed, no industry standard yet exists. Due to traditional practice and the competitive nature of last development and protection, most manufacturers continue to use their own sizing scales. This has resulted in the development of sizing methods with inconsistencies which prevent the development of a universal standard or even a consistent set of conversion factors long sought by international footwear distributors. What this means to the individual is that any 'size' provided by such a measuring device can be best interpreted as only a rough estimate or starting point to selection of mass produced footwear of varying manufacturer and local.

Regardless of the method used, in order to detect the pattern presented by a foot, some form of transducing medium is required. This is generally handled in one of two ways: (1) using one or more radiating transducers/transceivers which move physically across the sensing surface under control of synchronized servos or motors as realized in designs of U.S. Pat. No. 3,328,882 or using an array of numerous discrete stationary elements distributed the sensing plane as is realized in U.S. Pat. Nos. 4,294,014 and 5,323,650.

The first has the advantages of using a minimal number of transducers and associated control circuitry and theoretically infinite resolution. The disadvantages are the use of mechanical or electromechanical components which generally consume more power, are bulkier, less reliable and relatively more difficult to operate. The second has the advantages of simplified operation, compact design and enhanced reliability afforded by solid-state construction and disadvantages including a greater part count, use of discrete transducer elements, more complex control circuitry, finite resolution and more sophisticated manufacturing techniques.

The invention presented here is superior to previous designs because of its enhanced practicality achieved by using a distributed transducing medium.

SUMMARY OF THE INVENTION

In order to better understand the design details presented for this invention, a brief description of the operation is provided. Reference to conventional designs are also included, where instructive.

Aside from a more practical circuit design, the proposed device also takes greater advantage of MCU resources to make the unit more flexible and easier to use. This is achieved in three ways: (1) by storing a number of different standard sizing scales internally within the MCU ROM for enhanced versatility, (2) using the computational abilities of the MCU to provide additional fitting information and (3) use of a series of hardware interrupt routines to fully automate device operation.

Finally, hardware interrupts and a series of associated routines are employed to fully automate and simplify operation such that no user input is required. This also simplifies manufacturing and enhances reliability by eliminating the need for buttons, switches or other mechanical adjustments. This includes MCU wake up and sleep modes which help conserve power by monitoring use and automatically shutting off the display and all other nonessential circuit activity upon detecting a time out idle state. Also, option selection is further simplified by automated selection routines which use the display and sensor pad to prompt the user for input. If no user input is detected after prompting, the unit than automatically activates the most commonly used option as default. In the preferred embodiment, this includes the option of selecting among various established sizing systems including Mondopont, German Stich as well as the various subscales for gender and age upon power-up which automatically defaults to the U.S. system if no selection is specified.

Aside from facilitating operation, such an autonomous, self-managing algorithm also improves reliability by employing exclusive use of linked, autonomous code blocks supported by the time-out redirection and default parameters mentioned above. This fully automates operation such that the user is allowed to select options, while at the same time never actually possessing control of device operation. The aforementioned safeguards combined with the automated sleep/wake-up modes and internal watchdog routines all serve to improve reliability by insuring that the operation is relatively immune to faulty programming caused by ambiguous, invalid or unspecified input conditions, internal latch-ups, computation errors or improper control settings.

In summary, the present invention facilitates the sizing of mass produced footwear, while offering improved performance and efficiency over existing designs by using solid-state construction employing a distributed transducer medium connected directly to the MCU to reduce apparatus circuitry, reduce power consumption and provide a compact construction for portability. In addition, internal MCU routines are incorporated to enhance versatility and simplify use by automating operation, programming and option selection, while offering a selection of sizing scales and surplus sizing information.

The invention is described in detail on the basis of the following description, attached drawings and schematics.

DETAILED DESCRIPTION OF THE DRAWINGS

Figure 1:
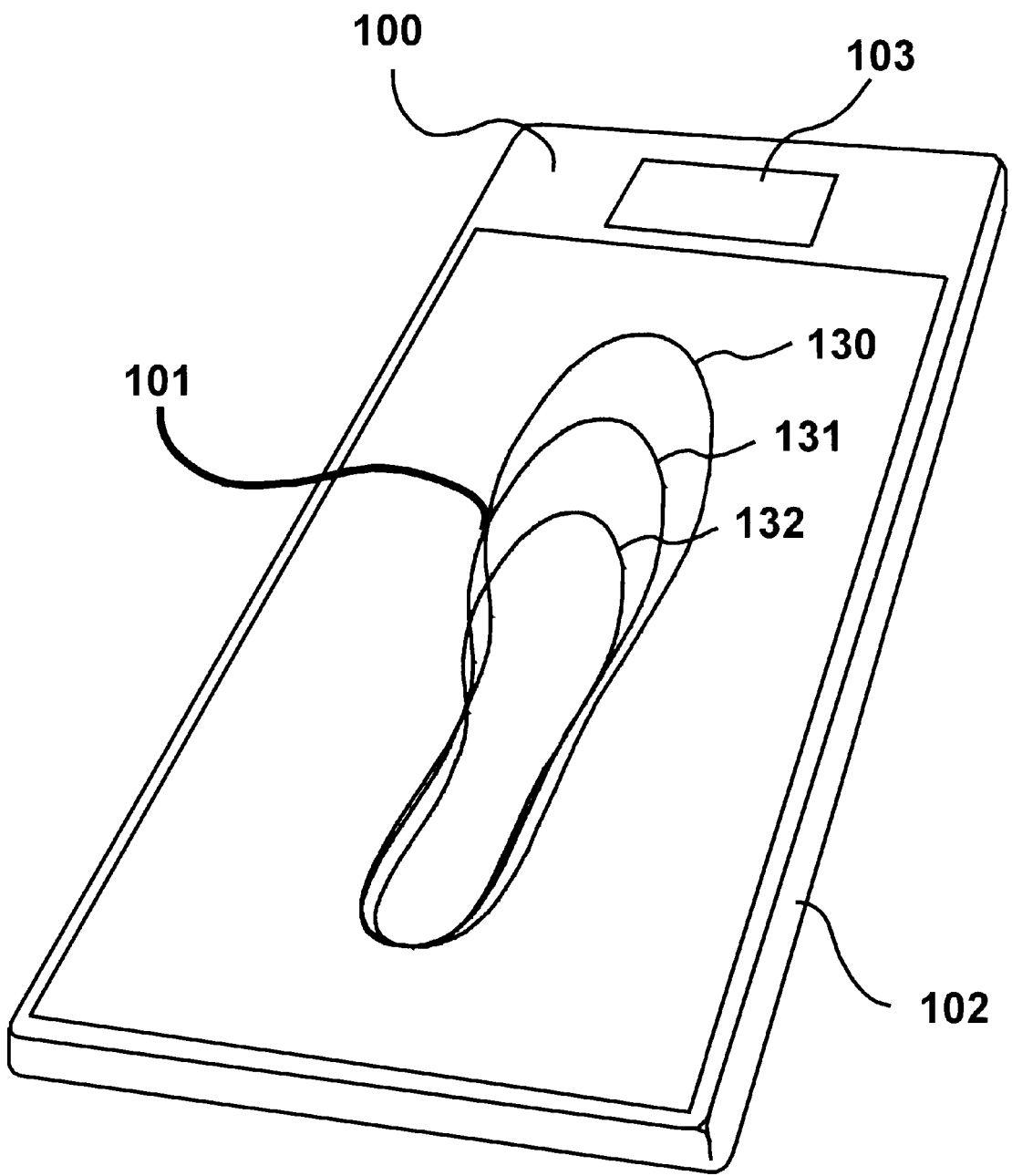
FIG. 1 is a general outline view of the apparatus.

As shown in FIG. 1, the preferred embodiment of the apparatus 100 includes a protective sensor pad 101 for placement of a foot, a liquid crystal display (LCD) 103 for displaying the corresponding sizing information, and a protective enclosure 102 for housing the respective parts.

Figure 2:
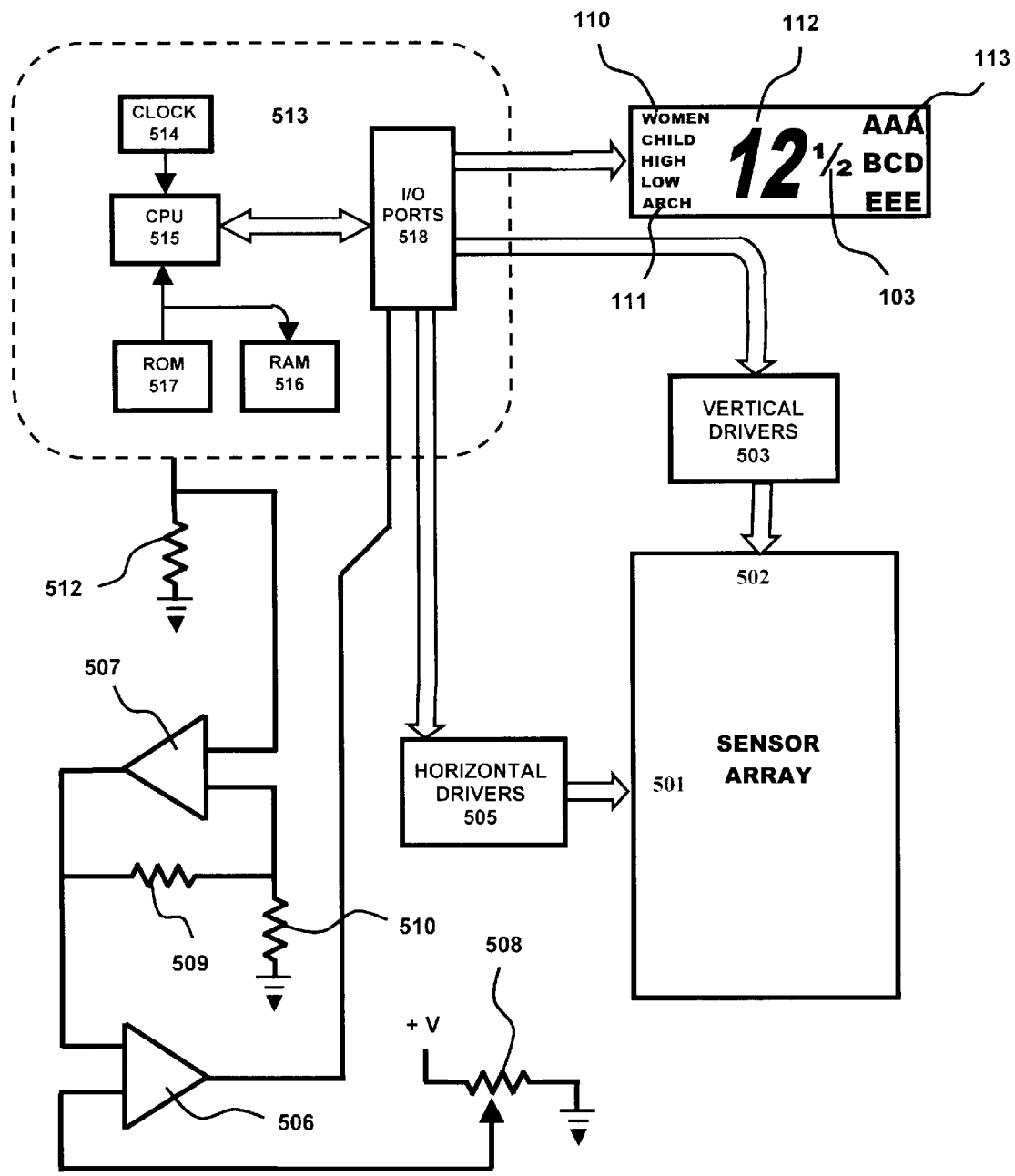
FIG. 2 is a block diagram of overall circuit schematic.

As shown in FIG. 2, the vertical 502 and horizontal 501 sensor arrays contain a series of distributed transducers connected to the vertical drivers 503 and horizontal drivers 505. Although either passive or reactive transducers may be used, the preferred design employs passive conductive elements driven by AC signals because it simplifies manufacturing, reduces cost, and enhances reliability by avoiding the tighter tolerances, conductive compounds, and coupling elements associated with the prior art designs. The passive conductive elements are driven by AC drive signals, which create the conditions required to drive the sizing medium to obtain a foot image.

Figure 3:
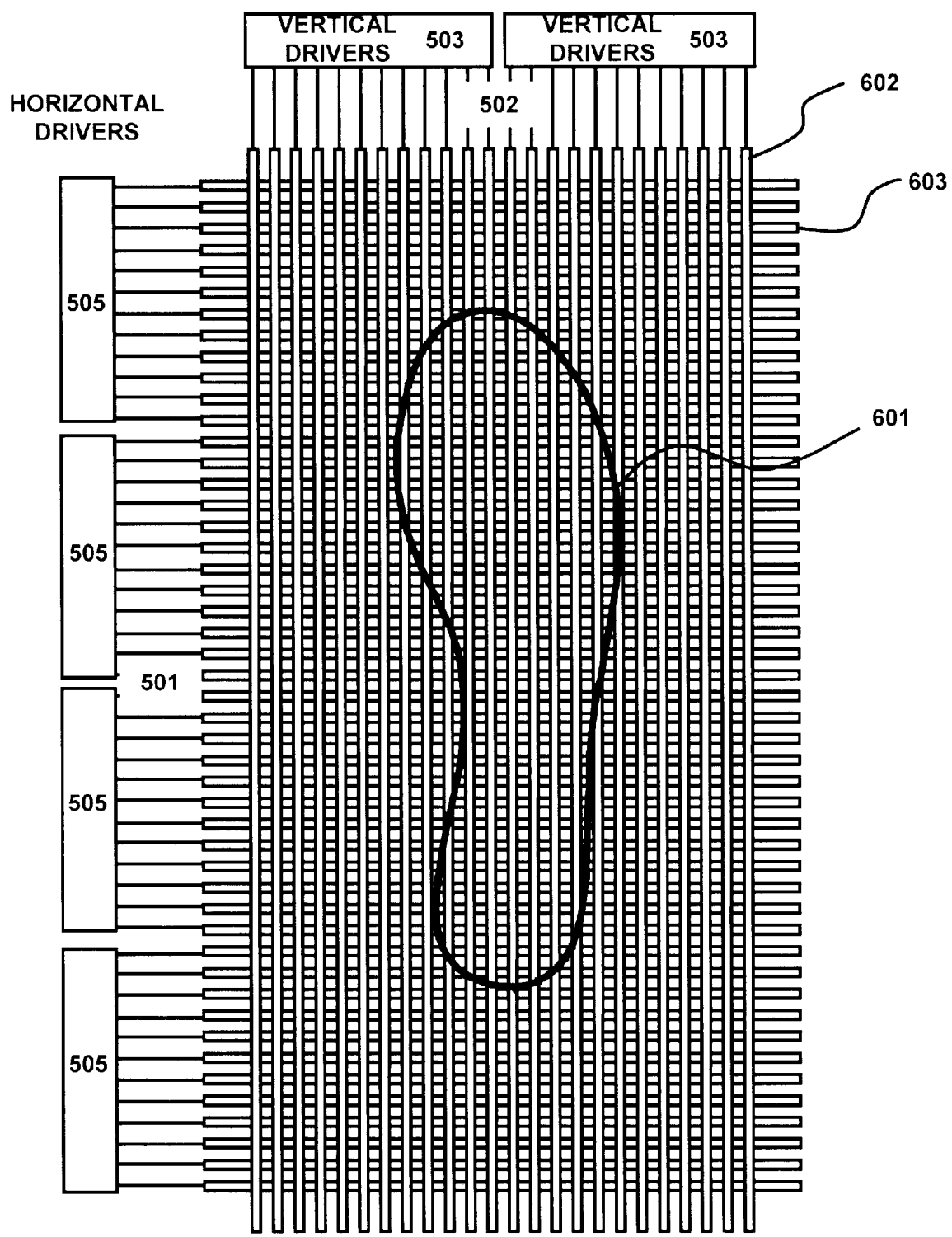
FIG. 3 is a schematic showing the sensor array and addressing circuit.

Referring now to FIG. 3, the sensor arrays 501 and 502 includes a plurality of horizontal and vertical conductive traces arranged in a contiguous fashion across the front and back of the sensing area. The sensor arrays 501 and 502 may be formed in various ways including silk screening conductive ink upon a mylar substrate or using a standard etched copper printed circuit board as utilized in the preferred embodiment. The etched copper printed circuit board (PCB) has the advantage of simplifying fabrication by allowing the sensor arrays 501 and 502 and the remaining circuitry to share the same PCB producing a single board unit in a single etching operation. The outline of a foot 601 (as shown on FIG. 3) having been placed on the sensor pad 101 is determined by detecting the change in impedance produced by the permitivity of the human foot where it lies in close proximity to the sensor arrays 501 and 502.

Therefore, by using a sensor arrays 501 and 502 comprising conductive elements such as 602 vertical element and 603 horizontal element of equal width and spacing.

It will be instructive now to discuss further the microcontroller 513 as shown in FIG. 2. The MCU 513 comprises a clock 514, the CPU 515, read only memory (ROM) 517, and random access memory (RAM) 516. Ideally, any device(s) providing basic arithmetic operations, data processing and storage will suffice, however in the preferred embodiment, a single chip VLSI microcontroller, providing all these functions on board, is preferred due to their relative economy, small package, minimal power consumption and availability. Specifically, the preferred embodiment employs a MCV that provides a generous 352 bytes of RAM, 15.9 KB of ROM, 31 I/O pins for driving up to 225 transducer elements and internal watchdog routines to improve reliability.

Electronic shoe sizing is accomplished in three steps: (1) obtaining foot length and width measurements by electronically scanning the foot surface, (2) scaling the measured values to the proper shoe size and (3) displaying the size. Although each part employs different task dedicated equipment, all are accomplished primarily by utilization of a programmable digital processor or multiprocessing unit (MCU) 513.

To conserve battery life, when not in use the unit 513 is maintained in a sleep mode in which all operations except memory retention are disabled. During this stage, all lines of the vertical array 502 located on the top side of the sensor plane are held in a static high state at full operating potential, while the horizontal array 501 on the back side are held at ground potential. Since all components are of CMOS technology, very little power is consumed until a foot is placed upon the pad. The increase is permativity afforded by the presence of a foot causes an increase in capacitance of the horizontal/vertical array configuration which, in turn, produces a transient voltage signal detected by the interrupt pin 514 of the MCU. This, then brings the MCU out of the sleep mode to begin a sizing operation.

The measuring cycle of the sizing operation is performed by scanning the foot sensor arrays 501 and 502 in the vertical and horizontal directions to obtain the length and width, respectively. The bottom or horizontal array 501 consists of a series of contiguous conductive traces separated by a distance equal to one-half shoe size, while the top or vertical array 502 consists of a series of contiguous conductive traces separated by a distance equal to one shoe width. Each trace is tied to an output of a horizontal or vertical driver 503, 505 which are in turn grounded through a reference impedance element 512. To measure length, all traces of the top or vertical array 502 are held 'low' near ground potential forming a virtual ground, while each trace of the bottom or horizontal array 501 is successively driven 'high' near full supply potential As the array is scanned, the voltage across the reference impedance element 512 is amplified by amplifier circuit 507, 509 and 510 are fed to a comparator 506 in the detecting circuitry. As each successive trace is made 'high', the MCU 513 increments an internal counter and checks the output of the comparator for a 'high' or 'low' condition. As a trace adjacent to a foot is encountered, the presence of the foot causes a local increase in permativity, which produces a transient current and resulting voltage rise across the reference impedence element 512 . If the voltage produced exceeds the trip point determined by the set point resistor 508 of the detecting circuitry, the comparator output switches from 'low' to 'high' signaling the MCU 513 that a foot edge, that is a toe or heel point, has been encountered. By storing the count for each corresponding comparator transition, the relative physical length of the foot may be determined expressed in the number of horizontal traces between toe and heel. Repeating the same scenario, scanning the traces of the top or vertical array 502 with the bottom or horizontal array 501 tied to ground, allows the physical width to be determined as expressed by the number of vertical traces between the sides of the foot. A variable resistor 508 may be used during testing to vary the trip point as needed to determine the optimum value accurate foot edge detection.

Sizing the foot consists of translating the corresponding physical dimensions obtained as described above into a standard last size using the appropriate sizing scale. This is accomplished automatically by the MCU 513 via an addresser. The addresser comprises software routines and embedded look-up tables internal to the MCU 513. The resulting size being dependent upon the scale utilized. i.e., Men, Women, Children, American, European, etc..

Finally, the calculated size is temporarily displayed on the device 103 directly from the MCU 513, showing both length and width. Note although the type of display utilized in reduction to practice is a liquid crystal display (LCD) employing numerical length and alphabetic width indicators shown, it is apparent that any scale and display technology employed may be employed as dependent upon the application and particular scaling or sizing custom dictates. Again, to conserve battery life in portable units, the size is displayed for a time determined by a present counter internal to the MCU 513 sufficient to registered by the user and then turned off. Another sizing operation is than performed and the cycle repeated. If no comparator 506 transitions are detected, i.e., no foot is present, the device 513 then returns to the low-power sleep mode until reawakened as described above.

Figure 4:
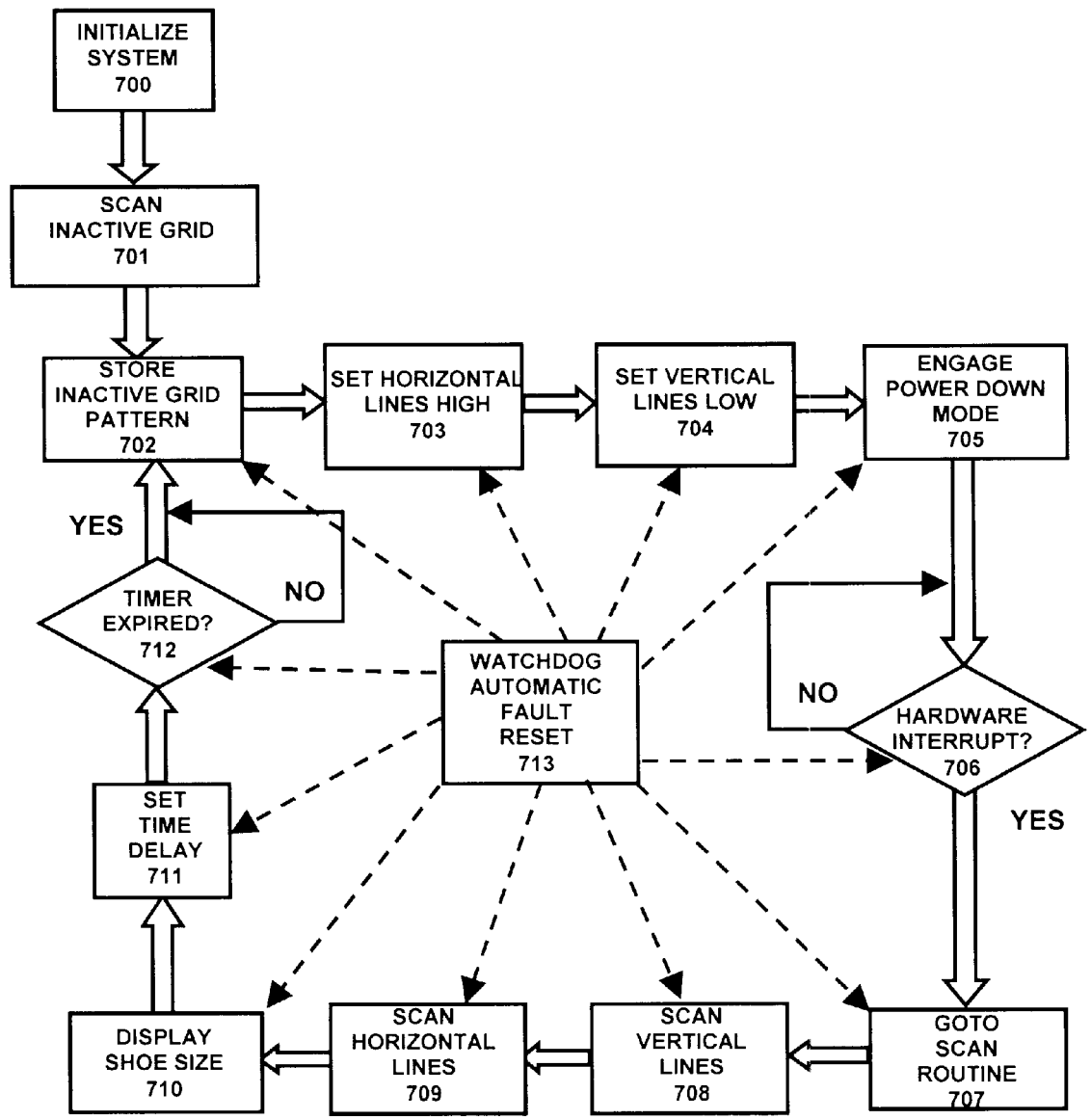
FIG. 4 is a flow diagram of the software and algorithms in the microcontroller.

Although the exact coding of the MCU program depends upon the specific MCU selected, a basic flow diagram used in construction of the preferred embodiment and generally applicable to most any MCU is shown in FIG. 4. Principle elements of the algorithm include the exclusive use of linked, autonomous code blocks supported by time-out redirection 706,712 and default parameters. This fully automates operation such that the user is allowed to select options, while at the same time never actually possessing control of device operation. Thus, combined with the automated sleep/wake-up operation and internal watchdog routines 713, shown dashed in FIG. 4, this serves to both simplify operation and improve reliability by ensuring operation is relatively immune to faulty programming caused by ambiguous, invalid or unspecified input conditions, internal latch-ups, computation errors or improper control settings.

The program is divided into three primary modes of operation (1) the power-up or initialization mode, (2) idle or sleep mode and (3) sizing mode. Upon power up, the apparatus first executes the initialization routine 700, which configures memory, register and I/O port settings and prompts the user to select the sizing scale desired. It then performs an initial sizing operation without a foot present to construct an electronic image of the sensor arrays 501 and 502 itself to identify and record sensor arrays 501 and 502 anomalies such as conductive element width variations, cracks and parasitic particles arising from non-ideal manufacturing processes, aging and normal wear and tear. This is then compared with actual sizing images during use to filter out such irregularities which may otherwise distort the measured image resulting in inaccurate sizing.

After initialization, the apparatus then enters the idle mode designed to reduce power consumption between sizing exercises. During this mode, the MCU 513 is placed in a sleep mode in which all internal operations except the memory retention is halted such that, a minimal current consumption is achieved, which prolongs battery life.

To further facilitate operation, transfer between idle and active sizing modes is done automatically by continuously monitoring the sensor pad for activity. When no activity is sensed before expiration of a preset time delay 711, the MCU 513 then automatically returns to the idle mode, enables the external interrupt and places a static potential across the sensor array 703, 704 which allows the unit to remain in a static, low current state, until activated by the level transition at the external interrupt pin of the MCU 706. This is caused by the transient charging current produced by the change ;in impedance resulting from the initial foot placement. This then initiates the interrupt, waking the MCU 513 and placing it in the active sizing mode. When brought out of the idle mode, the device automatically scans the sensing area for a foot image 707 through 710 and displays the corresponding size in accordance with the scale selected. Aside from the particular sizing system selected the device also can be made to automatically adjust to the proper sub-scale relating to gender and/or age without requiring adjustment by the user. This is achieved by dividing the sensor pad 101 into specific regions for men 130, women 131 and youth 132 as depicted in FIG. 1 and making absolute as well as relative measurements. Although foot size is determined with the foot placed anywhere within the sensor pad boundary by measuring the relative distance between heel and toe, automatic scale adjustment can be added by directing the user to place their heel in the appropriate region using labels 130,131,132 and display prompts 110 and measuring the absolute distance from the sensor arrays 501 and 502 edge. Thus, by detecting the proper scale placement, the apparatus is able to determine the proper scale automatically without user adjustment, thus providing optimum versatile, multipurpose operation, while still maintaining a simple and easy sizing procedure.

Those who are skilled in the art will readily perceive how to modify the present invention still further. Thus, many possible embodiments may be made of the present invention without departing from the scope thereof, it is to be understood that all matter herein set forth or shown in the accompanying drawings is to be interpreted as illustrative and not in a limiting sense. According the foregoing description should be regarded as only illustrative of the invention, whose full scope is measured by the following claims.

We claim:

1. A digital apparatus for measuring and analyzing a foot comprising:
    a digital medium to convert a foot position to electrical signals;
    a controller coupled to said digital medium for applying electrical signals to said digital medium and for processing said electrical signals to generate foot sizing data;
    a reference impedance element coupled with said controller for use by said controller as the reference for assessing the electrical status of the digital medium; and
    a display for displaying foot sizing data generated by the controller.

2. The apparatus of claim 1, wherein said digital medium comprises a horizontal sensor array connected to a horizontal driver, and a vertical sensor array connected to a vertical driver, and an addressor for addressing the sensor arrays for use in the controller.

3. The apparatus of claim 2, wherein said horizontal sensor array and said vertical sensor array comprise a plurality of conductive traces.

4. The apparatus of claim 2, wherein said addressor comprises:
    software routines and embedded look-up tables internal to said controller.

5. The apparatus of claim 1, wherein said controller, reference impedance element, and display are disposed on a circuit board.

6. The apparatus of claim 1, wherein said display is a liquid crystal display.

7. The apparatus of claim 1, wherein said reference impedance element comprises a reference resistor.

8. The apparatus of claim 7, wherein the voltage drop across said reference resistor is maintained low enough so as to not interfere with controller operation.

9. The apparatus of claim 1, wherein the controller is a single chip controller comprising:

a central processing unit for executing instructions controlling said scanning circuitry and for processing said data indicative of foot size;

a clock coupled to said central processing unit for synchronizing controller unit operations;

read only memory coupled to said central processing unit for storing routines, data, and subroutines of instruction to be executed by said central processing unit; and random access memory for storing measured data, transformed data, and calculated data of instructions to be executed by said central processing unit.

10. The apparatus of claim 3, wherein said display is connected in parallel with said sensor array, and wherein the impedance of said sensor array is less than the impedance of said display.

11. The apparatus of claim 1, further comprising:

a signal amplifier for amplifying electrical signals;

a protective enclosure for housing and protecting the controller, sensor array, reference impedance element, amplifier, analog to digital conversion circuit, and display; and, a sensor pad disposed within a upper portion of said protective enclosure for placement of a foot.

12. The apparatus of claim 1, wherein said controller is battery powered.

13. An apparatus for measuring and analyzing a foot for a man, woman, or youth, said apparatus comprising:

a digital medium configured to receive and transmit a plurality of electrical signals to convert a foot position of a man, woman, or youth to electrical signals;

a controller coupled to said digital medium to analyze the electrical signals to generate foot sizing data;

a reference impedance element coupled with said controller for use by said controller as the reference for assessing the electrical status of the digital medium;

a driver circuit;

a digital detector circuit; and a display for displaying foot sizing data generated by the controller.

14. The apparatus of claim 13, wherein said digital medium comprises a horizontal sensor array connected to a horizontal driver, and a vertical sensor array connected to a vertical driver, and a addressor for addressing the sensor array for use in the controller.

15. The apparatus of claim 14, wherein said sensor array comprise a plurality of conductive traces.

16. The apparatus of claim 14, wherein said addressor comprises:

software routines and embedded look-up tables internal to said controller.

17. The apparatus of claim 13, wherein said digital medium, controller unit, impedance element, signal amplifier, and said display are disposed on a circuit board.

18. The apparatus of claim 13, wherein said display is a liquid crystal display.

19. The apparatus of claim 13, wherein said reference impedance element comprises a reference resistor.

20. The apparatus of claim 19, wherein the voltage drop across said reference resistor is maintained low enough so as to not interfere with controller operation.

21. The apparatus of claim 13, further comprising:

a signal amplifier for amplifying electrical signals;

a protective enclosure for housing and protecting the controller, sensor array, reference impedance element, amplifier, analog to digital conversion circuit, and display; and, a sensor pad disposed within a upper portion of said protective enclosure for placement of a foot.

22. The apparatus of claim 13, wherein said controller comprises:

a central processing unit for executing instructions controlling said scanning circuitry and for processing said data indicative of foot size;

a clock coupled to said central processing unit for synchronizing controller unit operations;

read only memory coupled to said central processing unit for storing routines, data, and subroutines of instruction to be executed by said central processing unit; and random access memory for storing measured data, transformed data, and calculated data of instructions to be executed by said central processing unit.

* * * * *